United States Patent
Akatsu et al.

(10) Patent No.: US 10,864,018 B2
(45) Date of Patent: *Dec. 15, 2020

(54) METHOD FOR MANUFACTURING MEDICAL LINEAR MEMBER

(71) Applicant: SYNTEC CORPORATION, Iwaki-shi, Fukushima (JP)

(72) Inventors: Kazumi Akatsu, Fukushima (JP); Jack C. Chang, Logan, UT (US)

(73) Assignee: SYNTEC CORPORATION, Iwaki (JP)

( * ) Notice: Subject to any disclaimer, the term of this patent is extended or adjusted under 35 U.S.C. 154(b) by 209 days.

This patent is subject to a terminal disclaimer.

(21) Appl. No.: 15/749,804

(22) PCT Filed: Aug. 6, 2015

(86) PCT No.: PCT/JP2015/072388
§ 371 (c)(1),
(2) Date: Feb. 2, 2018

(87) PCT Pub. No.: WO2017/022124
PCT Pub. Date: Feb. 9, 2017

(65) Prior Publication Data
US 2018/0221057 A1   Aug. 9, 2018

(51) Int. Cl.
*A61B 17/68* (2006.01)
*A61B 17/58* (2006.01)
(Continued)

(52) U.S. Cl.
CPC .............. *A61B 17/68* (2013.01); *A61B 17/58* (2013.01); *A61B 17/84* (2013.01); *C22F 1/006* (2013.01);
(Continued)

(58) Field of Classification Search
CPC ......... A61F 2/82; A61B 17/84; A61B 17/842; A61B 17/58; A61B 2017/00526;
(Continued)

(56) References Cited

U.S. PATENT DOCUMENTS 5,562,725 A * 10/1996 Schmitt ...................... A61F 2/07
623/1.53
6,264,684 B1 * 7/2001 Banas ....................... A61F 2/82
623/1.13
(Continued)

FOREIGN PATENT DOCUMENTS

JP          10-033683        2/1998
JP       2010094150 A   *  4/2010
(Continued)

OTHER PUBLICATIONS

International Search Report, dated Oct. 6, 2015 (dated Oct. 6, 2015), 2 pages.

*Primary Examiner* — Keith Walker
*Assistant Examiner* — Benjamin C Anderson
(74) *Attorney, Agent, or Firm* — Rankin, Hill & Clark LLP

(57) ABSTRACT

A method of manufacturing a medical linear member includes a step of forming a first spiral body (1) whose cross-sectional shape is a substantially perfect circular shape by spirally winding a base body (3) having a plurality of arrayed wires (2) formed of a shape memory alloy, around a winding core (4), a step of performing a first shape memory process on the first spiral body (1), a step of cutting the first spiral body (1) into a first predetermined length, a step of removing the winding core (4) from the cut first spiral body (1), a step of forming a second spiral body (6) whose cross-sectional shape is a flat shape by compressing the first spiral body (1) in a diametral direction, and a step of performing a second shape memory process on the second spiral body (6).

4 Claims, 6 Drawing Sheets

(51) Int. Cl.
  *A61B 17/84* (2006.01)
  *C22F 1/00* (2006.01)
  *C22F 1/10* (2006.01)
  *A61B 17/00* (2006.01)

(52) U.S. Cl.
  CPC ...... *C22F 1/10* (2013.01); *A61B 2017/00526* (2013.01)

(58) Field of Classification Search
  CPC . H01B 5/08; H01B 5/10; H01B 5/102; H01B 5/104; H01B 5/107; H01B 13/0006; H01B 13/0285; H01B 13/0292; C22F 1/00; C22F 1/10; C22F 1/006
  USPC .............................. 148/563; 29/439; 264/230
  See application file for complete search history.

(56) References Cited

U.S. PATENT DOCUMENTS

| | | | | |
|---|---|---|---|---|
| 6,589,227 | B2* | 7/2003 | Sonderskov | A61B 17/12022 600/434 |
| 8,491,649 | B2* | 7/2013 | Mach | A61F 2/07 623/1.28 |
| 8,721,625 | B2* | 5/2014 | Klint | A61B 17/12022 600/434 |
| 10,524,938 | B2* | 1/2020 | Akatsu | A61F 2/82 |
| 2005/0090403 | A1* | 4/2005 | Raber | H01L 39/2487 505/100 |
| 2006/0060266 | A1* | 3/2006 | Bales | A61F 2/91 148/563 |
| 2009/0165898 | A1* | 7/2009 | Wong | A61L 31/022 148/402 |
| 2011/0022050 | A1* | 1/2011 | McClellan | A61B 17/823 606/74 |
| 2013/0060323 | A1* | 3/2013 | McHugo | A61F 2/90 623/1.18 |

FOREIGN PATENT DOCUMENTS

| | | | |
|---|---|---|---|
| JP | 2010-232009 | | 10/2010 |
| JP | 2010232009 | A * | 10/2010 |
| JP | 2011-136143 | | 7/2011 |
| JP | 2011136143 | A * | 7/2011 |
| JP | 2012-232027 | | 11/2012 |
| JP | 2012232027 | A * | 11/2012 |
| JP | 2014-161650 | | 9/2014 |

* cited by examiner

METHOD FOR MANUFACTURING MEDICAL LINEAR MEMBER

TECHNICAL FIELD

The present invention relates to a method for manufacturing a medical linear member.

BACKGROUND ART

In the related art, when surgery to incise a breastbone is performed, a medical linear member whose cross-sectional shape is a flat shape is used in order to close the breastbone after the surgery. For example, as the medical linear member whose cross-sectional shape is the flat shape, a medical linear member is known in which a plurality of filaments is braided into a flat string shape (for example, refer to Patent Literature 1).

CITATION LIST

Patent Literature

Patent Literature 1: Japanese Patent Application Laid-Open No. 2012-232027

SUMMARY OF INVENTION

Technical Problem

However, the medical linear member having the flat string shape is formed by braiding the plurality of filaments. Consequently, when the medical linear member is manufactured, the filaments may be rubbed with each other, thereby causing a disadvantage that the medical linear member is likely to be worn.

The present invention is made in order to solve the disadvantage, and an object thereof is to provide a method capable of manufacturing a medical linear member which is not worn when manufactured and which has a flat cross-sectional shape.

Solution to Problem

In order to achieve the object, there is provided a method of manufacturing a medical linear member according to the present invention. The method includes a step of forming a first spiral body whose cross-sectional shape is a substantially perfect circular shape by spirally winding a base body having a plurality of arrayed wires formed of a shape memory alloy, around a winding core formed of a round bar, at intervals in an array direction, a step of performing a first shape memory process by heating the first spiral body, a step of cutting the first spiral body into a first predetermined length, a step of removing the winding core from the cut first spiral body, a step of forming a second spiral body whose cross-sectional shape is a flat shape by compressing the first spiral body from which the winding core is removed, into a substantially perfect circular shape in a diametral direction, and a step of performing a second shape memory process by heating the second spiral body.

In the manufacturing method according to the present invention, first, a member having the plurality of arrayed wires formed of the shape memory alloy is used as the base body. The base body is spirally wound around the winding core at intervals in the array direction, thereby forming the first spiral body. In this case, the winding core is formed of the round bar. Accordingly, the first spiral body has the substantially perfect circular shape along an outer shape of the winding core.

Next, the first spiral body is heated so as to perform the first shape memory process. The first shape memory process allows the first spiral body to have a memory of a spirally wound shape having the intervals in the array direction.

Next, the first spiral body is cut into the first predetermined length. For example, the first predetermined length is set to be a length suitable for compression in the subsequent step.

Next, the winding core is removed from the cut first the spiral body. Since the winding core is removed, the first spiral body can be compressed in the diametral direction of the substantially perfect circular shape in the subsequent step.

Thereafter, the first spiral body from which the winding core is removed is compressed in the diametral direction of the substantially perfect circular shape. As a result, the second spiral body having the flat cross-sectional shape is formed from the first spiral body.

Next, the second spiral body is heated so as to perform the second shape memory process. The second shape memory process allows the second spiral body to have a memory of the flat cross-sectional shape. In this manner, it is possible to obtain the medical linear member having the flat cross-sectional shape.

Heating for the second shape memory process can be performed simultaneously when the first spiral body is compressed. However, if the heating is performed after the first spiral body is compressed and the second spiral body is formed, it is possible to reduce stress on the obtained medical linear member.

According to the manufacturing method of the present invention, the base body having the plurality of arrayed wires is spirally wound around, thereby forming the first spiral body having the substantially perfect circular cross-sectional shape. The first spiral body is compressed so as to form the second spiral body. Accordingly, it is possible to manufacture the medical linear member which is not worn due to braiding and which has the flat cross-sectional shape.

In addition, in the manufacturing method according to the present invention, it is preferable to further cut the medical linear member obtained as described above into the second predetermined length. For example, the second predetermined length is the length of the medical linear member used for actual treatment. Accordingly, the medical linear member obtained using the manufacturing method according to the present invention can be easily used for the treatment.

In addition, in the manufacturing method according to the present invention, it is preferable that the first spiral body is compressed by placing the first spiral body heated by the first shape memory process, on a base while a heated state is maintained, and by pressing a compression member from above. In this case, the first spiral body cut into the first predetermined length maintains the heated state. Accordingly, the first spiral body is likely to be deformed, and can be easily compressed.

In addition, in the manufacturing method according to the present invention, it is preferable that the compression member is pressed by a spring member which biases the compression member in a direction toward the first spiral body. The compression member can be pressed using hydraulic pressure. However, when the first spiral body, maintains the heated state, there is a possibility that a device used for the hydraulic pressure may be damaged due to heat.

However, according to the spring member, it is possible to press the compression member without being damaged due to the heat.

DESCRIPTION OF EMBODIMENTS

Next, an embodiment according to the present invention will be described in more detail with reference to the accompanying drawings.

Figure 1:
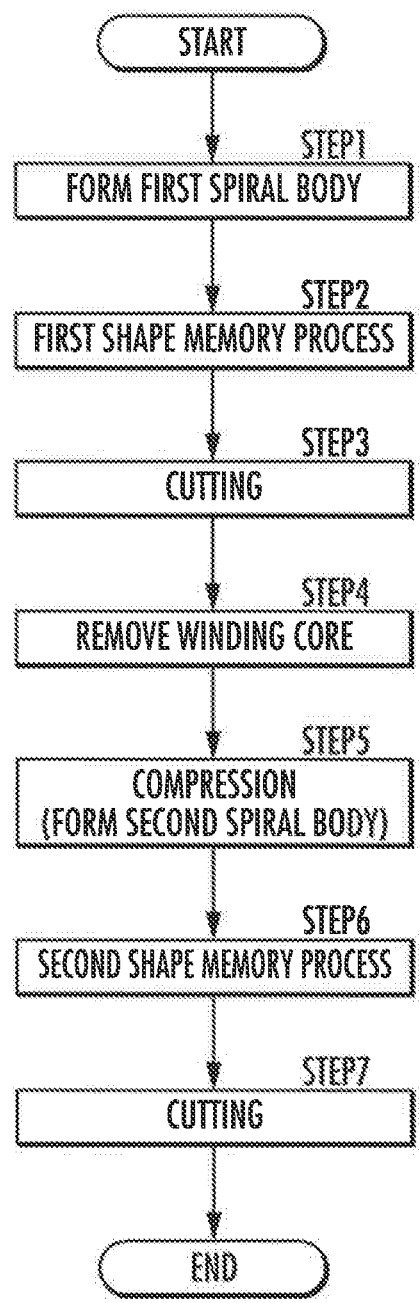
FIG. 1 is a flowchart illustrating a step of manufacturing a medical linear member according to the present invention.

As illustrated in FIG. 1, in a manufacturing method according to the present embodiment, a first spiral body 1 is first formed in STEP 1. The first spiral body 1 is formed by spirally winding a base body 3 having a plurality of wires 2 formed of a shape memory alloy and arrayed parallel to each other, around a winding core 4 formed of a round bar.

In this case, the base body 3 is spirally wound at an interval S in an array direction. As the shape memory alloy configuring the wires 2, a nickel-titanium alloy or a nickel-titanium-cobalt alloy can be used.

Next, in STEP 2 in FIG. 1, a first shape memory process is performed on the first spiral body 1. For example, in the first shape memory process, the first spiral body 1 in a state where the base body 3 is spirally wound around the winding core 4 is accommodated in a heating furnace (not illustrated), and is held at the temperature of 150° C. to 900° C. for 3 to 120 minutes. The wire 2 is formed of the shape memory alloy. Accordingly, through the above-described process, the first spiral body 1 is allowed to have a memory of a spirally wound shape having the interval S in the array direction.

If the first shape memory process is completed, the first spiral body 1 is taken out from the heating furnace. After the first spiral body 1 is cooled, the first spiral body 1 is cut into a length of 3 to 100 cm, for example, a length of 30 cm in STEP 3 in FIG. 1. Next, the winding core 4 is removed therefrom in STEP 4.

Figure 3A:
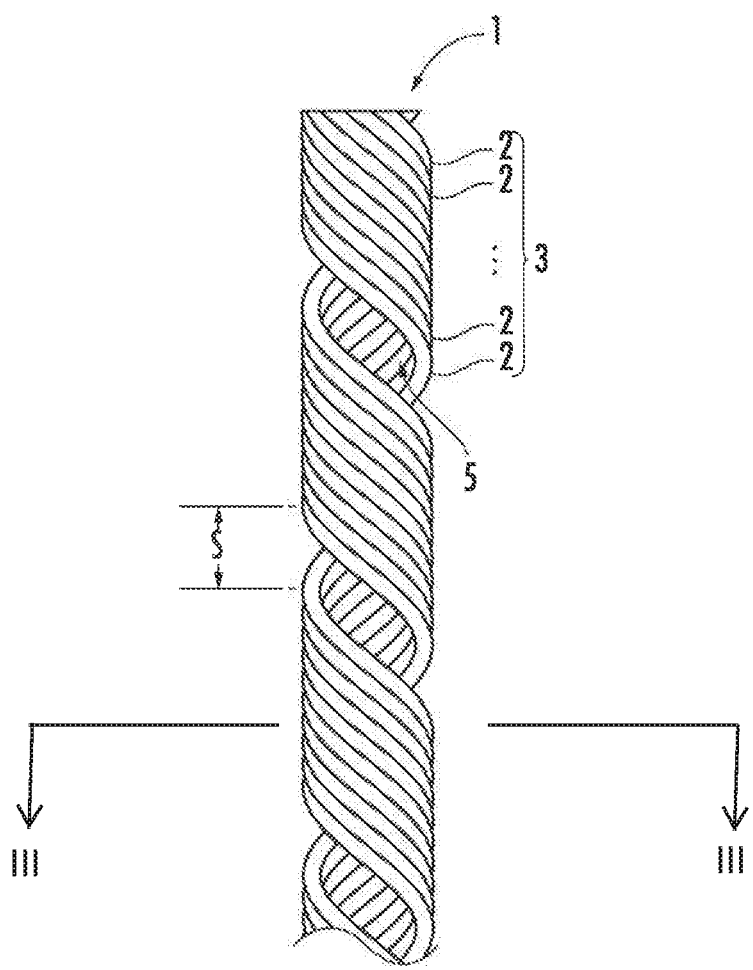
FIG. 3A is a plan view illustrating a configuration of the first spiral body.
Figure 3B:
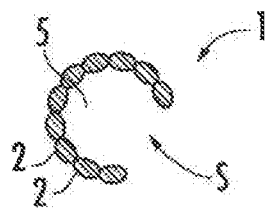
FIG. 3B is a sectional view taken along line III-III in FIG. 3A.

As a result, as illustrated in FIG. 3A, the base body 3 having the plurality of wires 2 arrayed parallel to each other is spirally wound at the interval S in the array direction, thereby obtaining the first spiral body 1 which internally has a space portion 5. In this case, as illustrated in FIG. 3B, the first spiral body 1 has a substantially perfect circular cross-sectional shape.

Figure 4:
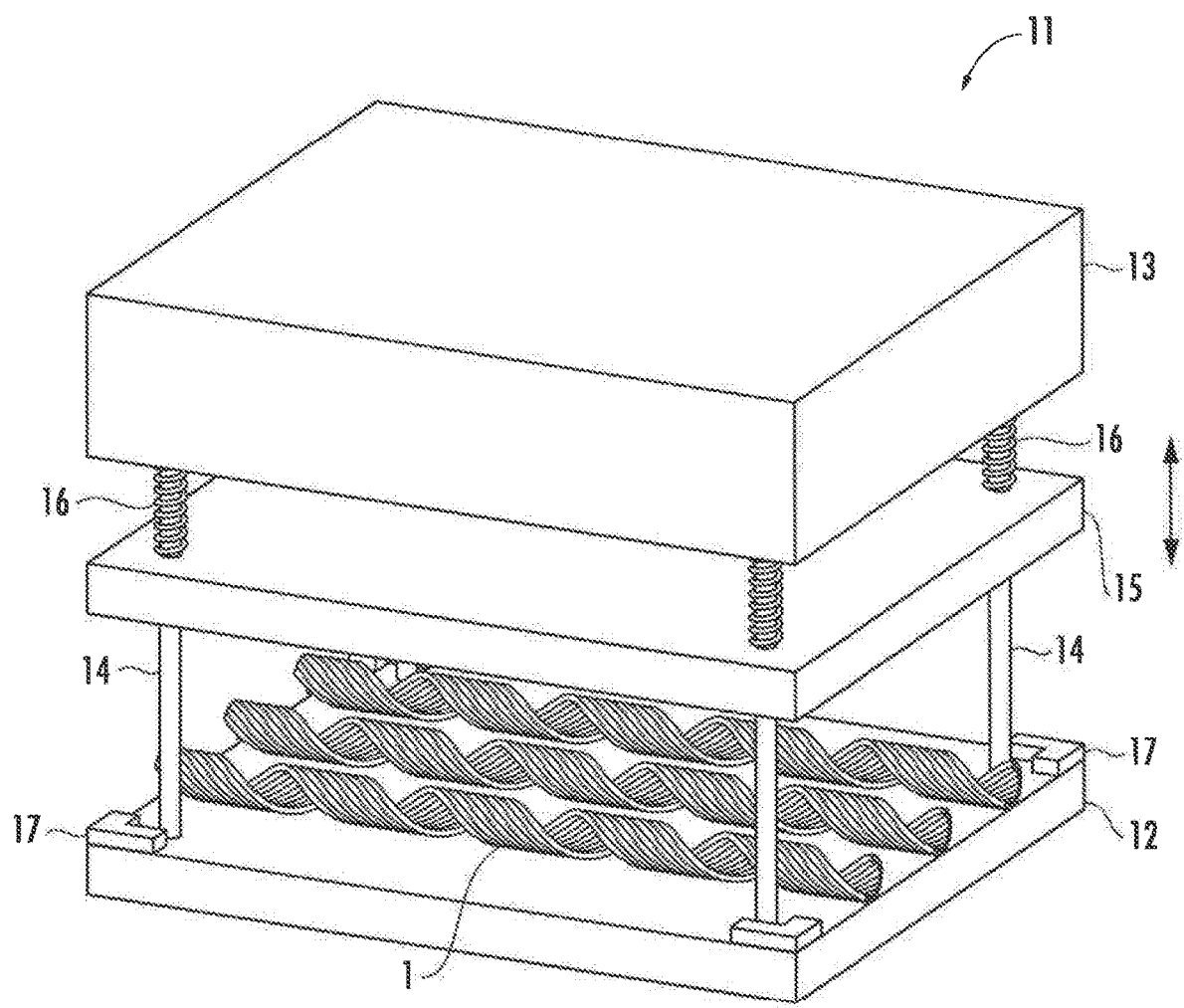
FIG. 4 is a perspective view illustrating a configuration of a compression jig for compressing the first spiral body.

Next, in STEP 5 in FIG. 1, the first spiral body 1 is compressed in a diametral (radial) direction of the substantially perfect circular shape. The first spiral body 1 is compressed using a compression jig 11 illustrated in FIG. 4.

The compression jig 11 includes a slide bar 14 disposed between a base 12 and a top plate 13, and a plate-shaped press member 15 slidable and movable up and down along the slide bar 14. Each of the base 12, the top plate 13, and the press member 15 has a square shape whose one side is 30 cm in a plan view, and the slide bar 14 is disposed at four corners of the square shape. In addition, the press member 15 is biased in a direction toward the base 12 by a spring member 16 installed on an outer peripheral side of the slide bar 14.

When the first spiral body 1 is compressed using the compression jig 11, first, in a state where the press member 15 is moved to the top plate 13 side against a biasing force of the spring member 16, a spacer 17 is disposed at the four corners on the base 12. A thickness of the spacer 17 is selected depending on a target compression degree.

Next, the first spiral body 1 is placed on the base 12. The first spiral body 1 can be placed on the base 12 by avoiding the spacer 17 so that a plurality of pieces is parallel to each other, and at intervals so as not to interfere with each other when compressed. Although the number of the first spiral bodies 1 placed on the base 12 depends on a diameter thereof, the number is usually in a range from several pieces to ten-odd pieces.

Figure 5:
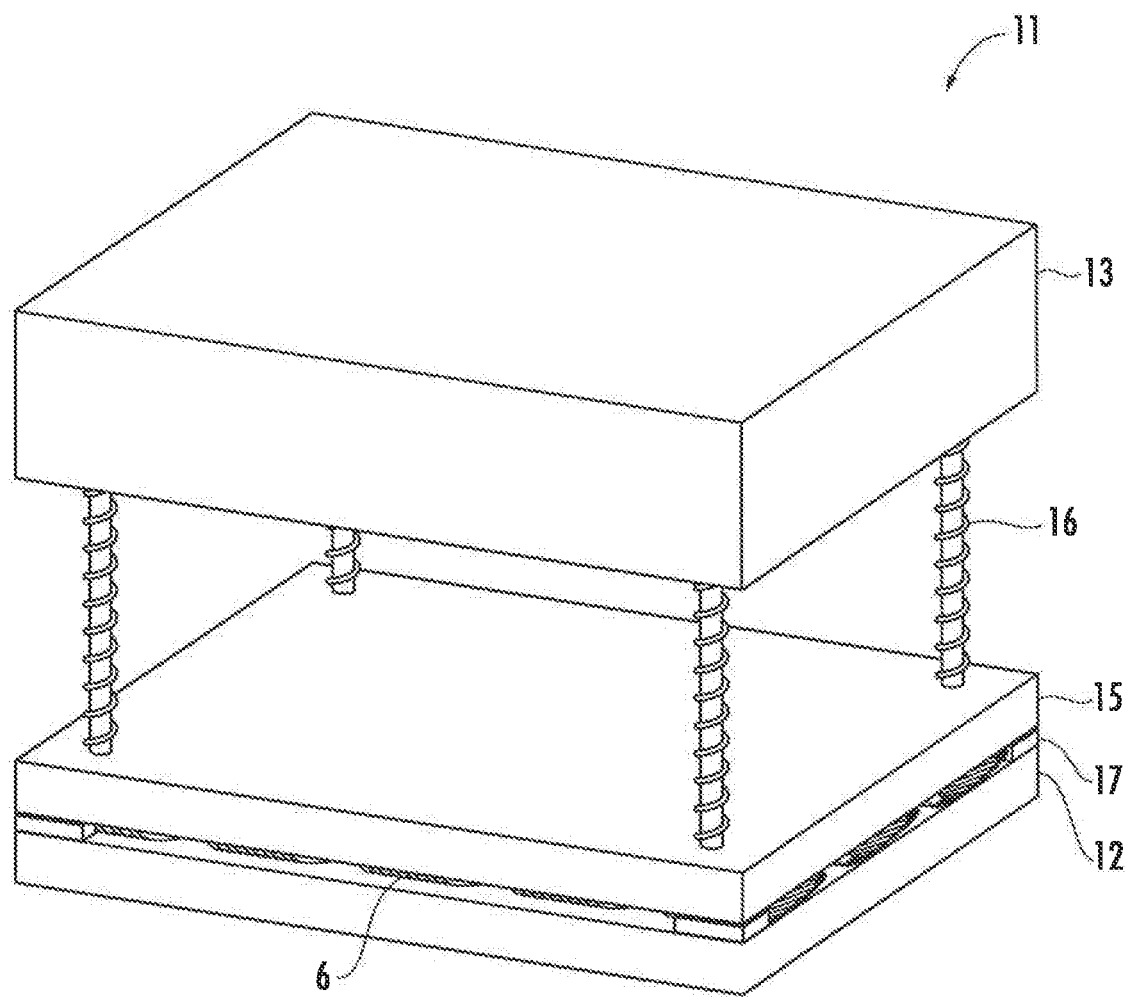
FIG. 5 is a perspective view illustrating a state where the first spiral body is compressed using the compression jig illustrated in FIG. 4.

Next, as illustrated in FIG. 5, the press member 15 moved to the top plate 13 side is pressed against the first spiral body 1 placed on the base 12 by using the biasing force of the spring member 16. As a result, the first spiral body 1 is compressed in the diametral direction of the substantially perfect circular shape by the press member 15, thereby forming the second spiral body 6 illustrated in FIG. 6. As illustrated in FIG. 5, the press member 15 is stopped to move to the base 12 side on an upper surface of the spacer 17. Accordingly, a thickness of the second spiral body 6 is determined in accordance with a thickness of the spacer 17.

Figure 6A:
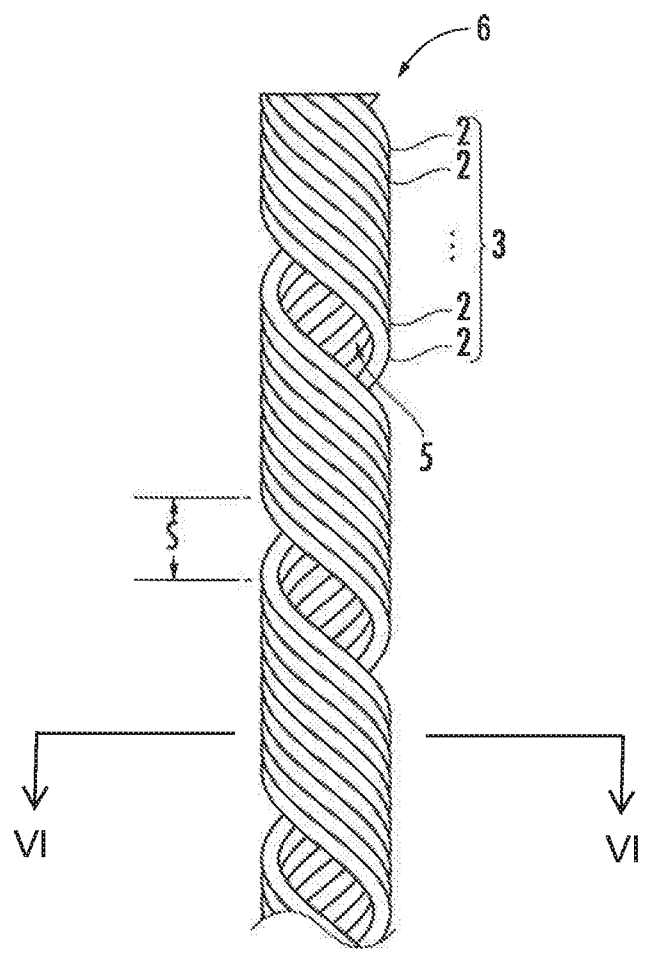
FIG. 6A is a plan view illustrating a configuration of a second spiral body.
Figure 6B:
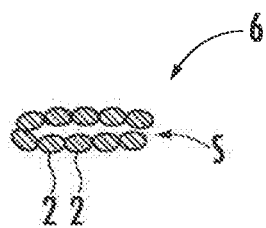
FIG. 6B is a sectional view taken along line VI-VI in FIG. 6A.

As illustrated in FIG. 6A, in the second spiral body 6, the base body 3 having the plurality of wires 2 arrayed parallel to each other is spirally wound at the interval S in the array direction. The second spiral body 6 is the same as the first spiral body 1 in that the second spiral body 6 internally has the space portion 5. However, as illustrated in FIG. 6B, the second spiral body 6 has a flat cross-sectional shape.

Next, in STEP 6 in FIG. 1, a second shape memory process is performed on the second spiral body 6. For example, in the second shape memory process, the second spiral body 6 in a state of having the flat cross-sectional shape is accommodated in a heating furnace (not illustrated), and is held at the temperature of 150° C. to 900° C. for 3 to 120 minutes. The wire 2 is formed from the shape memory alloy. Accordingly, through the above-described process, the second spiral body 3 is allowed to have a memory of the flat cross-sectional shape.

Figure 2:
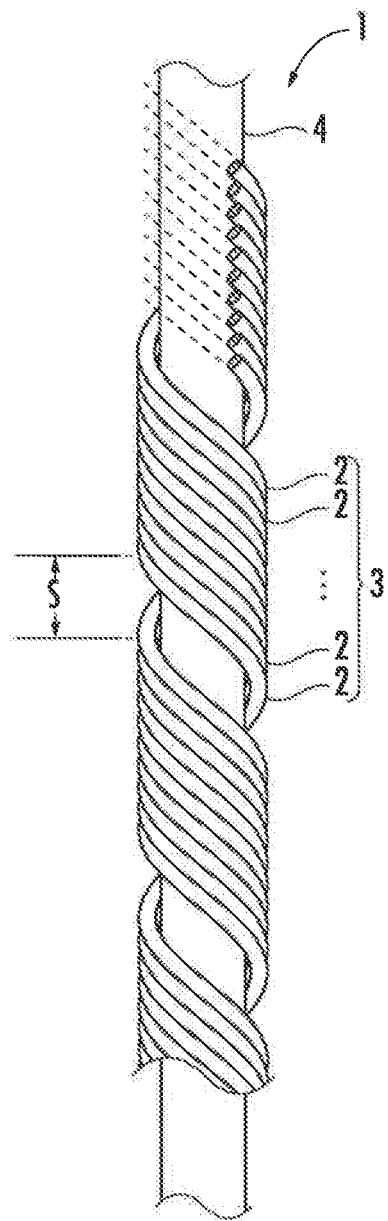
FIG. 2 is a plan view illustrating a method of forming a first spiral body.

Next, in STEP 7 in FIG. 2, the second spiral body 6 subjected to the second shape memory process is cut into a length of 30 to 50 mm. In this manner, it is possible to obtain the medical linear member according to the present embodiment.

In the present embodiment, an example has been described in which the spiral bodies 1 and 6 are formed from the base body 3 having only one layer. However, the spiral bodies 1 and 6 may include a configuration in which a plurality of the base bodies 3 is stacked with respect to an axis thereof. In addition, in this case, the base bodies 3 and 3 stacked adjacent to each other may have spiral directions opposite to each other.

DESCRIPTION OF REFERENCE NUMERALS 1 first spiral body
2 wire 3 base body
4 winding core
5 space portion
6 second spiral body
11 compression jig
16 spring member

The invention claimed is:

1. A method of manufacturing a medical linear member, the method comprising:
   a step of forming a first spiral body whose cross-sectional shape is a perfect circular shape by spirally winding a base body having a plurality of arrayed wires formed of a shape memory alloy, around a winding core formed of a round bar, at intervals in a direction along an axial length of the winding core;
   a step of performing a first shape memory process by heating the first spiral body;
   a step of cutting the first spiral body into a first predetermined length;
   a step of removing the winding core from the cut first spiral body;
   a step of forming a second spiral body whose cross-sectional shape is a flat shape by compressing the first spiral body from which the winding core is removed, in a diametral direction of the substantially perfect circular shape; and
   a step of performing a second shape memory process by heating the second spiral body.

2. The method of manufacturing a medical linear member according to claim 1, further comprising:
   a step of cutting the second spiral body subjected to the second shape memory process, into a second predetermined length.

3. The method of manufacturing a medical linear member according to claim 1,
   wherein the first spiral body is compressed by placing the first spiral body heated by the first shape memory process, on a base while a heated state is maintained, and by pressing a compression member from above.

4. The method of manufacturing a medical linear member according to claim 3,
   wherein the compression member is pressed by a spring member which biases the compression member in a direction toward the first spiral body.

* * * * *